(12) United States Patent
Yomtov et al.

(10) Patent No.: US 8,608,635 B2
(45) Date of Patent: Dec. 17, 2013

(54) TET SYSTEM FOR IMPLANTED MEDICAL DEVICE

(75) Inventors: Barry Yomtov, Marblehead, MA (US); John Robert Batty, Miami, FL (US)

(73) Assignee: HeartWare, Inc., Miami Lakes, FL (US)

( * ) Notice: Subject to any disclaimer, the term of this patent is extended or adjusted under 35 U.S.C. 154(b) by 1098 days.

(21) Appl. No.: 12/584,776

(22) Filed: Sep. 10, 2009

(65) Prior Publication Data

US 2010/0063347 A1    Mar. 11, 2010

Related U.S. Application Data

(60) Provisional application No. 61/191,595, filed on Sep. 10, 2008.

(51) Int. Cl.
*A61M 1/12*    (2006.01)
(52) U.S. Cl.
CPC ..................................... *A61M 1/127* (2013.01)
USPC ............................................ 600/17; 623/3.28
(58) Field of Classification Search
USPC ........... 607/33, 61; 600/16–18; 623/3.1, 3.12, 623/3.27, 3.28
See application file for complete search history.

(56) References Cited

U.S. PATENT DOCUMENTS

| 4,665,896 | A | * | 5/1987 | LaForge et al. .................. 600/17 |
| 4,670,771 | A | | 6/1987 | Neidig et al. |
| 5,342,408 | A | | 8/1994 | deCoriolis et al. |
| 5,613,935 | A | * | 3/1997 | Jarvik ............................. 600/16 |
| 6,149,683 | A | | 11/2000 | Lancisi et al. |
| 7,167,756 | B1 | * | 1/2007 | Torgerson et al. .............. 607/61 |
| 2003/0171792 | A1 | | 9/2003 | Zarinetchi et al. |
| 2004/0039423 | A1 | * | 2/2004 | Dolgin ............................. 607/27 |
| 2005/0107847 | A1 | * | 5/2005 | Gruber et al. ................... 607/61 |
| 2007/0265703 | A1 | * | 11/2007 | Sutton et al. ................... 623/3.1 |

OTHER PUBLICATIONS

International Preliminary Report on Patentability issued by the International Bureau of WIPO on Mar. 15, 2011 in connection with International Application No. PCT/US2009/005108.
Written Opinion of the International Searching Authority issued by the International Searching Authority (ISA/US) on Nov. 12, 2009 in connection with International Application No. PCT/US2009/005108.
International Search Report issued by the International Searching Authority (ISA/US) in connection with International Application No. PCT/US09/05108, Nov. 12, 2009.
Written Opinion of the International Searching Authority issued by the International Searching Authority (ISA/US) in connection with International Application No. PCT/US09/05108, Nov. 12, 2009.
First Office Action issued Feb. 27, 2012 in connection with Israeli Patent Application No. 211320 filed Feb. 20, 2011.

(Continued)

*Primary Examiner* — Carl H Layno
*Assistant Examiner* — Jessica Sarcione
(74) *Attorney, Agent, or Firm* — John P. White; Cooper & Dunham LLP (57) ABSTRACT

A TET system is operable to vary an amount of power transmitted from an external power supply to an implantable power unit in accordance with a monitored condition of the implantable power unit. The amount of power supplied to the implantable power unit for operating a pump, for example, can be varied in accordance with a cardiac cycle, so as to maintain the monitored condition in the power circuit within a desired range throughout the cardiac cycle.

18 Claims, 9 Drawing Sheets

(56) References Cited

OTHER PUBLICATIONS

Response to First Office Action filed Dec. 26, 2012 in connection with Israel Patent Application No. 211320 filed Feb. 20, 2011.

First Examiner's Report issued Aug. 30, 2012 in connection with Canadian Patent Application No. 2,734,775 filed Feb. 18, 2011.
Response to First Examiner's Report filed Feb. 28, 2013 in connection with Canadian Patent Application No. 2,734,775 filed Feb. 18, 2011.

* cited by examiner

FIG. 4
TET SYSTEM - IMPLANTED TET BLOCK DIAGRAM

TET SYSTEM FOR IMPLANTED MEDICAL DEVICE

This application claims priority of U.S. Provisional Application No. 61/191,595, filed Sep. 10, 2008, the entire content of which is hereby incorporated by reference herein.

BACKGROUND OF THE INVENTION

The present invention relates to a transcutaneous energy transfer (TET) system and a TET system method of operation.

Transcutaneous energy transfer (TET) systems are used to supply power to devices such as heart pumps implanted internally within a human body. An electromagnetic field generated by a transmitting coil outside the body can transmit power across a cutaneous (skin) barrier to a magnetic receiving coil implanted within the body. The receiving coil can then transfer the received power to the implanted heart pump or other internal device and to one or more batteries implanted within the body to charge the battery.

One of the challenges of such systems is insufficient battery lifetime. The implanted battery may be required to supply the implanted device's entire power demand for one to several hours at a time, such as when the patient does activities that preclude wearing the external TET power unit, such as showering or swimming. When the implanted battery is first implanted into the patient, the battery capacity is large and can meet the power demand for the required amount of time. However, when subjected to frequent charging and discharging, the implanted battery's capacity decreases. With decreased battery capacity, the patient cannot spend as much time without the external TET power unit. Eventually, the battery may need to be replaced so that the patient can go without the external TET power unit for long enough periods of time again.

Until now, premature wear-out of the implanted battery due to frequent charging and discharging of the battery was believed to be unavoidable. Conventional TET systems do not supply power closely in accordance with the time-varying power requirements of implanted devices. As a result, when the implanted device has rapidly fluctuating power demands such as characteristic of circulatory assist pumps including left ventricle assist devices ("LVADs"), the implanted battery is required to supply power for momentary high power demands and the TET system recharges the battery when the momentary power demands ease.

SUMMARY OF THE INVENTION

In accordance with an aspect of the invention, a TET system is provided for powering an implanted electrical device. In a particular example, a circulatory assist device can be provided which can include one or more electrical devices such as a pump having an electric motor, the pump having a power demand which varies with the cardiac cycle of a patient in which the pump is implanted.

An implantable power unit is adapted for mounting within the body of the patient. The power unit may have a secondary coil and a power circuit connected to the secondary coil for controlling and supplying power to controlling circuitry and to the pump, for example. In that way, power can be received at the secondary coil and applied to controlling circuitry and to the pump. In one embodiment, a monitoring circuit of the implantable power unit can be used to monitor a condition of the power circuit. The monitoring circuit can transmit a transcutaneous telemetry signal which represents the monitored condition for use by a control circuit of an external unit to adjust power transmission.

An external power supply may be adapted for transcutaneous inductive coupling with the secondary coil, and may have a drive circuit operable to apply an alternating current to the primary coil, and a control circuit operable to receive the telemetry signal and adjust the alternating current in the primary coil at least in part in response to the telemetry signal. In a particular embodiment, the monitoring circuit and control circuit may be operable to monitor the condition of the power circuit and adjust the alternating current in the primary coil in accordance therewith. In that way, the alternating current in the primary coil may be varied substantially in accordance with the cardiac cycle.

DETAILED DESCRIPTION

Figure 1:
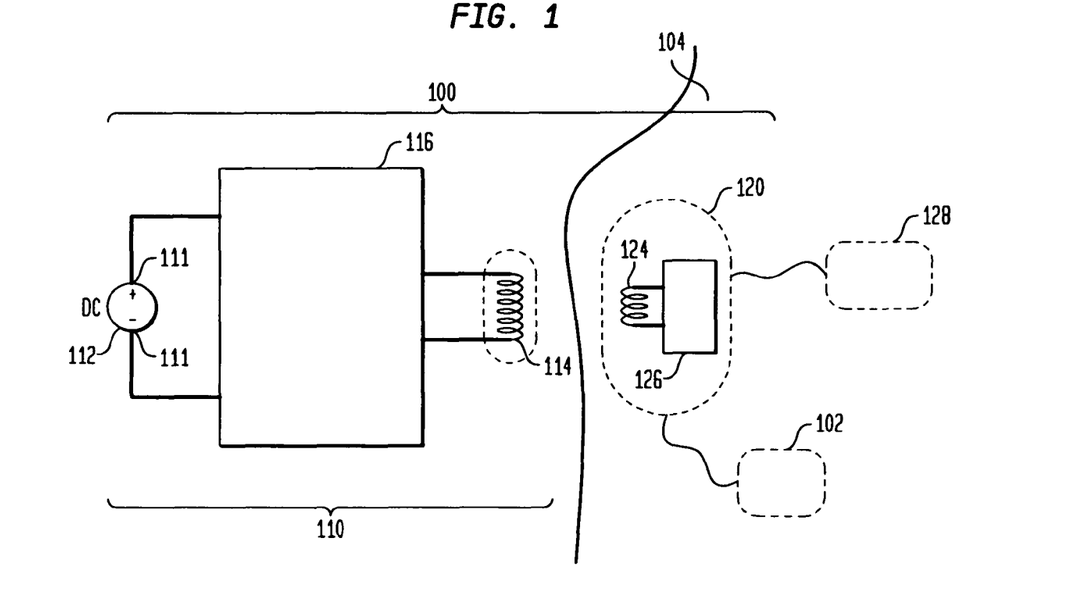
FIG. 1 is a partial cutaway sectional diagram illustrating components and operation of a TET system in accordance with an embodiment of the invention.

FIG. 1 schematically illustrates a transcutaneous energy transfer (TET) system 100 used to supply power to an implanted therapeutic electrical device 102 in an internal cavity within the body, i.e., below the skin of a patient 104. The implanted electrical device 102 can include a pump such as for use in pumping blood as a ventricular assist device ("VAD"), for example. The implanted electrical device 102 can include controlling circuitry to control, for example, a pump.

As depicted in FIG. 1, the TET system 100 includes an external module 110 having a primary power coil 114, associated circuitry 116 and terminals 111 for receiving an external source 112 of power. An internal module 120 implanted underneath the skin of the patient 104 has a secondary power coil 124, associated circuitry 126 and an output cable for supplying power to the implanted electrical device 102. Power is transferred from the primary coil 114 to the secondary coil 124 by means of inductive coupling, i.e., via near-field interaction of a magnetic field overlapping the primary 114 and secondary 124 coils. The voltage across each coil can be large, for example, peak-to-peak voltages of 100 V to 400 V are not uncommon. The implanted module 120 is also connected to an implanted battery 128 for supplying power to the implanted electrical device 102 in case power to the external module 110 when power transmission is interrupted between the external 110 and implanted 120 modules. With the implanted battery 128 as a backup, the external TET module 110 can be disconnected when the patient bathes or performs other activities.

Figure 2:
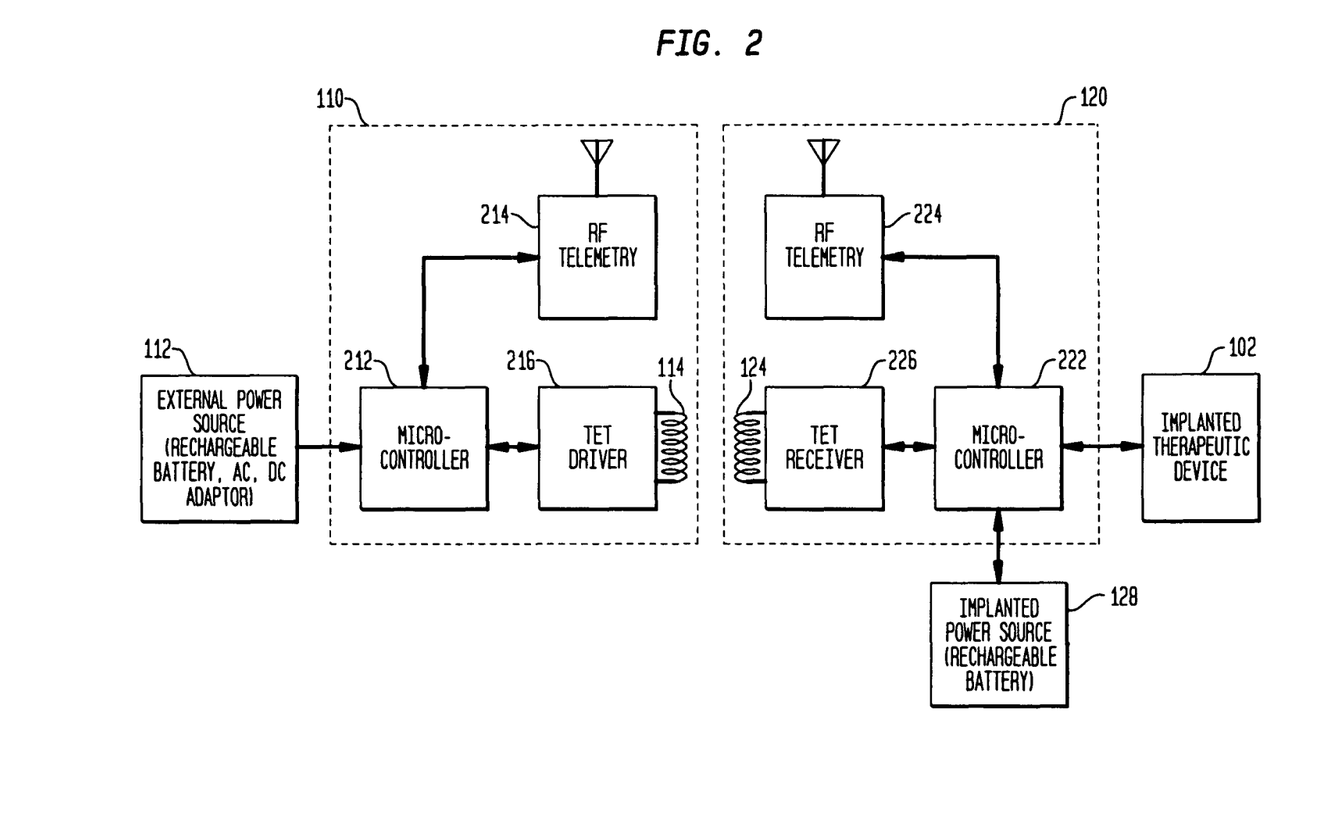
FIG. 2 is a block and schematic diagram further illustrating external and internal components of a TET system in accordance with an embodiment of the invention.

FIG. 2 is a functional block diagram illustrating electrical components of the TET system 100. As illustrated therein, the external module 110 of the TET system 100 includes the primary coil 114 and associated circuitry including a microcontroller 212, a radio frequency ("RF") telemetry system 214 and a TET driver 216. To reduce losses due to skin effect, the primary coil 114 can be fabricated using Litz wire, in which the primary coil 114 is made up of relatively thin, insulated wires twisted or woven together in groups. Power transfer from an external power source 112 to the implanted module 120 is provided through the TET driver 216 as controlled by microcontroller 212.

The implanted module 120 includes a TET receiver 226 including the secondary coil 124, a microcontroller 222 and an RF telemetry system 224. Like the primary coil 114, the secondary coil 124 can also be fabricated using Litz wire. The TET receiver 226 includes rectifier circuitry, such as a diode bridge, for converting electrical energy at the secondary coil in alternating current ("AC") form into direct current ("DC") form. DC power output from the TET receiver 226 is supplied to a microcontroller 222 of the implanted module 120, an implanted battery 128 and an implanted electrical device 102. The implanted electrical device 102 can include one or more of a variety of devices such as a VAD blood pump, for example, which has power demands which could not be supplied by the implanted battery 128 for long periods of time. In such case, the implanted battery 128 is not a primary power source, but is used to supply power for relatively short periods of time in case of an interruption in the transmission of power to the implanted module 120. For example, the implanted module 120 can rely on battery power when the patient takes a shower.

Figure 3:
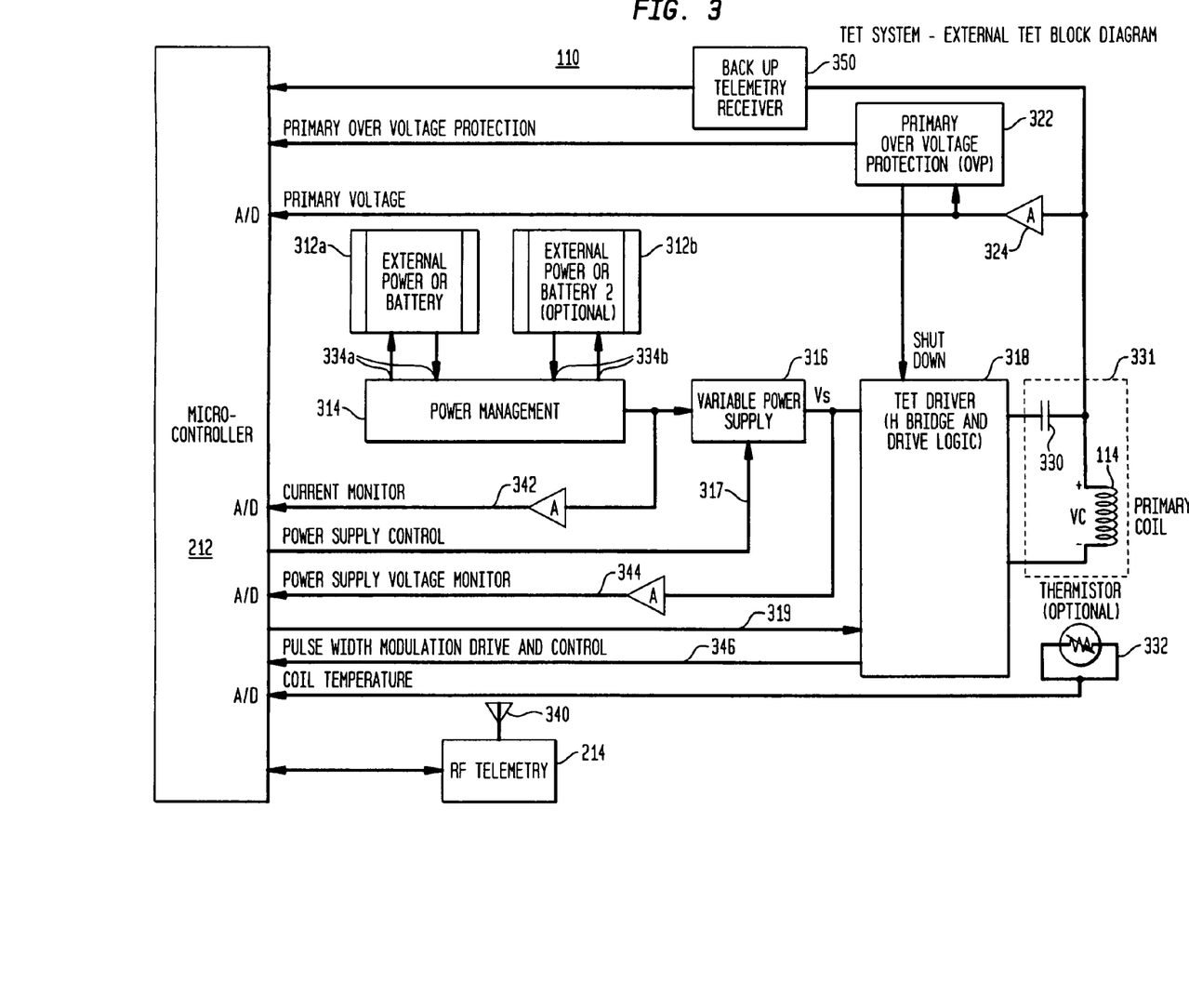
FIG. 3 is a block and schematic diagram further illustrating components of an external module of a TET system in accordance with an embodiment of the invention.

FIG. 3 is a block and schematic diagram illustrating operational components of the external module 110 in greater detail. As illustrated therein, a power management module 314 under control of microcontroller 212 transfers power in DC form to a variable output level power supply 316 from one or more external power sources 312a, 312b. The external power sources 312a, 312b can include one or more batteries, or one battery and an external AC/DC converter coupled to an AC source (such as a wall outlet) or a DC source, such as from within an automobile, for example.

The power management module 314 regulates the flow of power from the one or more external power sources 312a, 312b to a variable output power supply 316. This power module 314 has terminals 334a for connection with a first external power source 312a and has terminals 334b for connection with a second external power source 312b. The power module 314 may have more sets of terminals (not shown) for connection with power sources (not shown) other than sources 312a, 312b. The power management module 314 can determine which particular sources or types of sources are connected thereto and may also detect to which sets 334a, 334b of terminals the power sources 312a, 312b are connected. Module 314 determines whether or not power sources are connected thereto and may also determine the status of each connected power source, i.e., the voltages of each power source and the charge state of battery power sources. The power management module 314 also selects one or more of several connected power sources to draw power from in supplying energy to drive the TET system 100. For example, when both a battery and an AC or DC power source other than a battery are connected, power module 314 may use the AC or DC power as a primary source to power the external TET 110 and hold the battery in reserve for use in case the primary source becomes disconnected. The power management module 314 can also be used to regulate the flow of a charging current to one of the external power sources 312a, 312b, such as when the second power source 312b is a battery.

The variable power supply 316 provides power to a TET driver 318 at a rate which is subject to vary in accordance with the time-varying need for power of the electrical implanted therapeutic device 102 (FIG. 2). The power transfer rate to the TET driver 318 can be varied by modifying the voltage Vs at which power is output by the power supply 316 under control of one or more signals output by microcontroller 212. In one example, the output voltage Vs can be varied between 13 V and 25 V, in order to adjust between varying power demands and supply power efficiently to the TET driver 318.

The TET driver 318 supplies an excitation current to the primary coil 114 for transferring power to the implanted TET module 120. The TET driver 318 receives power at a steady (DC) supply voltage Vs and generates a magnetic flux for power transmission which has an AC waveform at a relatively low radio frequency (RF). Typically, the frequency of the AC power transmission waveform is set between about 30 kilohertz (kHz) and 300 kilohertz. Power is transmitted by inductive near-field coupling between the primary coil 114 and the secondary coil 124 (FIG. 2) of the implanted module 120.

The primary coil 114 is connected in series with a capacitor 330 in a tank circuit 331. The tank circuit 331 resonates at a resonant frequency determined by the inductance value of the coil 114 and the capacitance value of capacitor 330. The TET driver 318 includes a set of power-rated field effect transistors in an H-bridge arrangement, e.g., MOSFETs, which drive the primary coil 114 in a push-push fashion under control of logic drive circuits.

The TET driver 318 can regulate the transfer of power between the primary coil 114 and the secondary coil 124 (FIG. 2) in three ways. The TET driver 216 can output an excitation current to the primary coil 114 in a pulsed manner and vary the width of the drive pulses supplied to the coil 114 and hence, the duty cycle of such pulses. The TET driver 216 can also vary the frequency at which drive pulses are supplied to the primary coil 114 to create a desired balance between efficiency of power transfer throughout the system and stability of power regulation in the system. In addition, as mentioned above, the supply voltage Vs at which power is provided to the H-bridge circuit can be varied.

As further shown in FIG. 3, the external module 110 can include a thermistor 332 situated in the vicinity of the primary coil 114 for detecting a temperature of the coil 114 and providing a signal representative of the temperature to microcontroller 320. If the temperature increases to an excessive level which is uncomfortable or unsafe to the patient, the microcontroller 212 can alert the patient about possible coil misalignment. To allow the temperature to return to a more normal level, when possible, the microcontroller 212 can temporarily alter the operating mode of the implanted module 120 to reduce power requirements, such as by suspending charging of the implanted battery 128.

As further illustrated in FIG. 3, the external module 110 includes an over-voltage protection (OVP) circuit 322 having an input coupled to an amplifier 324 to receive a signal representative of a voltage Vc across the primary coil 114. OVP 322 detects when Vc reaches an excessive level and provides a signal to TET driver 318 to shut off the TET driver 318 until Vc reaches a safe level again. In one embodiment, OVP 322 is a hardware-controlled circuit, i.e., one which responds to the over-voltage condition on its own through operation of internal electrical circuitry, which may include hard-wired logic circuits. Therefore, OVP 322 responds rapidly to an over-voltage condition without requiring software instructions to be retrieved and executed within OVP 322. This circuit typically also does not need to await signals or instructions from microcontroller 212 to respond.

The external module 110 further includes a bi-directional radio frequency (RF) telemetry block 214 having a bi-directional signal interface with the microcontroller 212. The telemetry block 214 is arranged to transmit and receive signals through a transceiver and attached antenna 340. The telemetry block 214 is arranged to accept signals output by the microcontroller 212 for controlling operation of the implanted module 120, as will be described further below. The telemetry block 214 also receives various signals transmitted by a corresponding transceiver 224 (FIG. 2) of the implanted module 120 for monitoring operation of the implanted module 120.

The microcontroller 212 uses information received through the link between the telemetry modules 224, 214 of the implanted module 120 (FIG. 2) and the external module 110, as well as a signal 342 representative of supply current, a signal 344 representative of the supply voltage Vs and a signal 346 representative of the coil voltage Vc in order to variably supply energy in an efficient manner to the primary coil 114 and to address safety concerns.

Figure 4:
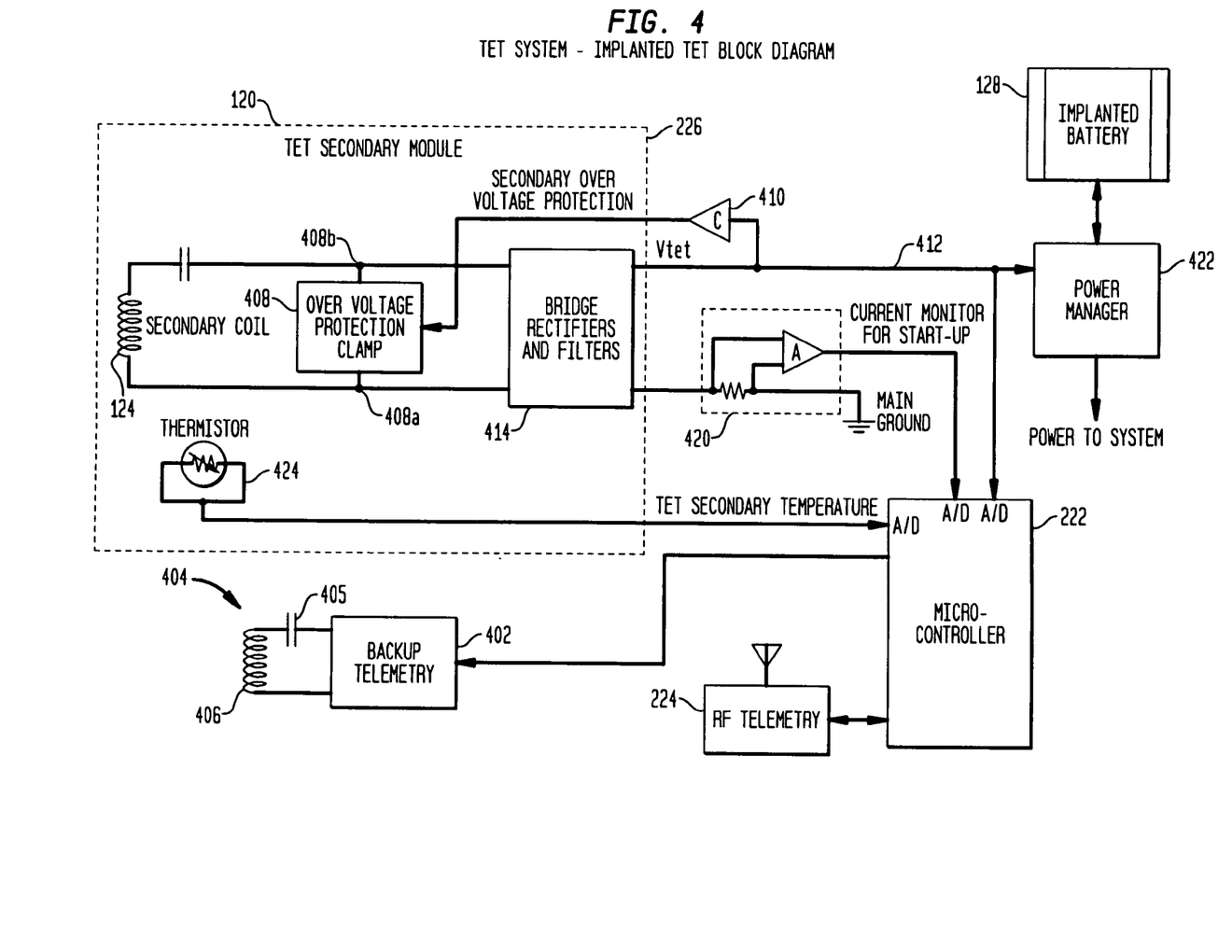
FIG. 4 is a block and schematic diagram further illustrating components of an implanted module of a TET system in accordance with an embodiment of the invention.

FIG. 4 is a block and schematic diagram further illustrating components of the implanted module 120 in accordance with an embodiment of the invention. As mentioned above, the implanted module 120 has a microcontroller 222 for controlling its operation, particularly with respect to the operation of the TET power receiver 226 through which power is received from the external module 110. The implanted module 120 also has an RF telemetry block 224 and a backup telemetry block 402. The RF telemetry block 224 includes a radio frequency transceiver used to transmit signals representative of measurements of operational parameters of the implanted module 120 and to receive signals from the external module 110 for controlling operation of the implanted module 120. A backup telemetry module 402 having a resonant tank circuit 404 including a capacitor 405 and an inductive data coil 406 separate from the secondary coil 124 is available to transmit the signals representing measured parameters from the implanted module 120 to the external module 110. Thus, the backup telemetry module 402 can transmit signals to the backup telemetry receiver 350 in the external module 110 (FIG. 3) by inductive coupling between the coil 406 and the primary coil 114 of the external module 110. In a particular embodiment, the backup telemetry module 402 can transmit signals in an inductively coupled manner to the backup telemetry receiver 350 in accordance with technology as specified in ISO 14443 or a further development thereof known as "Near Field Communication" ("NFC") as specified by the NFC Forum, Inc. Such technologies can be advantageous for transmitting signals short distances (e.g., less than 20 centimeters) at relatively low frequencies.

The resonant frequency and size of this inductive data coil 406 can be set for efficient operation at a frequency between the relatively low frequency (typically below 300 kHz) used for power transmission by way of coils 114, 124 and a standard transmission frequency (approximately 400 MHz) at which signals are normally transmitted between the RF telemetry transceivers 224, 214 (FIG. 3). In one example, the transmission frequency of the backup telemetry module 402 is about 10 megahertz (MHz). In one example, the backup telemetry module 402 may be capable to transmitting signals at a frequency designated for Near Field Communication of 13.56 megaHertz.

The backup telemetry module 402 need not be always active. In one embodiment, the backup telemetry module 402 is active only when the bi-directional RF telemetry system is unavailable or ineffective in communicating measurements of operational parameters between the microcontroller 222 of the implanted module 120 and the microcontroller 212 (FIG. 3) of the external module 110. For example, the backup telemetry module 402 can be utilized when signals representing up-to-date operational parameters for the implanted module 120 are not reaching the microcontroller 212, such as due to malfunction of the RF telemetry block 224 or due to interference in transmitting outbound signals over the primary link between RF telemetry blocks 224 and 214 (FIG. 3). In this context, interference can occur as "out-of-band" interference in which noise and emissions are present on the airwaves which make receiving signals from the RF telemetry block 224 more difficult. In-band interference can also occur, in which several similar devices are competing to transmit their signals over the same bandwidth. In one example, multiple transmitters can be operating at the same time and place in implanted devices of patients such as in an intensive care unit. For example, the implanted medical devices can transmit signals over a designated frequency band in accordance with the standard "Medical Implant Communications Service (MICS)." Interference can occur when too many devices are competing to use the allocated bandwidth at the same time. When devices are competing to use the same bandwidth, the amount of time each device can utilize the bandwidth may be reduced. In such case, when data loads to be transmitted from the implanted module 120 to the external module 110 are too great for the amount of time allocated on the bandwidth, it becomes difficult to transmit the signals representing the operational parameters for the implanted module 120.

When significant interference is present, the backup telemetry module 402 can be utilized in place of the regular RF telemetry block 114 to transmit data from the implanted module 110. When the interference is over, operation of the backup telemetry module 402 can be halted and transmission can resume from the primary RF telemetry block 214.

In one embodiment, the backup telemetry module 402, when active continuously and repetitively transmits the present valid power regulation data. The external TET controller 212 temporarily interrupts the power transmission drive pulses to TET driver 216. During this pause the backup telemetry receiver 350 of FIG. 3 listens for the low level backup telemetry signals. In this way, the backup telemetry receiver block 350 can receive low-power (millivolt level) backup telemetry signals in intervals between power transmission drive pulses which normally produce large wide band noise transients in the primary 114 and secondary 124 coils.

Transmission of the operational measurement signals by the backup telemetry module 402 can be performed by causing the resonant (carrier) frequency of the tank circuit 404 to be pulsed in a digitally encoded manner. For example, the carrier frequency of the tank circuit 404 can be switched on and off in succession using a pulse position modulation scheme. Stated another way, the carrier frequency of the tank circuit 404 can be pulsed, then paused for a relatively short period of time, then pulsed again to transmit a symbol indicating a digital value such as "0". In such example, the carrier frequency can also be pulsed, then paused for a longer period of time and then pulsed again to indicate a different type of symbol, such as "1" in a binary signalling scheme of "1's" and "0's", for example. The number of transmitted pulses and the number and placement of shorter and longer pauses between them can be used to represent different transmitted symbols.

Referring to FIG. 4, the TET receiver 226 outputs a supply voltage Vtet on line 412 to a power manager 422. The supply voltage Vtet is a variable voltage which can be controlled in order to vary the amount of power (i.e., current) being supplied to a motor controller or to the implanted battery 128 under different demand conditions. The microcontroller 222 may help to maintain Vtet at a higher voltage when higher power demands are present. In such case, as described below, the microcontroller 222 can transmit a signal back to the external module 110 to increase the rate of power transmission and in so doing, cause the voltage Vtet to increase. On the other hand, if the supply voltage Vtet is too high, the microcontroller 222 may help to reduce Vtet to a lower voltage when lower power demands are present. Again, the microcontroller 222 can transmit a signal back to the external module 110 to reduce the rate of power transmission and cause the voltage Vtet to fall.

The TET receiver 226 includes over-voltage protection circuitry 408 activated in case of an excessively high DC voltage level output by the TET receiver 226. The over-voltage protection circuitry 408 may be an over-voltage protection clamp. An excessive DC voltage can occur when the rectified AC current greatly exceeds the DC current demand of the implanted device. Implant power regulation is achieved by controlling the amount of current delivered to the load (implanted device) while maintaining a given voltage range. The drive level to the TET driver 216 and the primary coil 114 is modulated to provide the desired load current to the implanted module 120 at the specified voltage range. While the clamp 408 is active, the telemetry signals to the external TET 110 will reduce the drive levels to restore proper current output. Clamping the output voltage prevents damage to the implant system and increase reliability. Over voltage clamping normally occurs after a large step decrease in load current such as during pump start-up sequences.

A comparator 410 connected to receive the DC output voltage Vtet can detect when the DC output voltage exceeds a predetermined over-limit threshold. A signal output by the comparator 410 then activates the over-voltage protection circuitry 408, causing an immediate reduction in the DC output voltage Vtet. The over-voltage protection circuitry 408 remains active until the output voltage Vtet drops below a second predetermined threshold which is substantially lower than the predetermined over-limit threshold. When the lower threshold is crossed, the over-voltage protection circuitry 408 turns off again and the circuitry 414 resumes outputting the DC voltage Vtet as normal. In one example of operation, the supply voltage Vtet may be kept at a level of around 16 V. The over-limit threshold may be set to 25 V and the lower threshold for resuming operation may be set to 20 V. In such case, the over-voltage protection clamp 408 is intended to operate only from time to time when Vtet goes well beyond the normal range. One event likely to activate the over-voltage protection circuitry 408 is a step decrease in the power demand of the implanted module 120. Such decrease can occur, for example, when the power manager 422 turns off battery charging (because the implanted battery 128 is now fully charged) or the start-up demand of the motor of a high-wattage implanted electrical device subsides. Cessation of operation of such device might also cause the voltage Vtet to spike.

In one embodiment, the power circuit of the implantable unit further includes an overvoltage protection element operable to connect a shunt across the input of the rectifier if the voltage at the output of the rectifier exceeds the overvoltage value, the overvoltage protection element being operable to disable the power circuit if the voltage at the output of the rectifier exceeds a predetermined overvoltage value and re-enable the power circuit if the voltage at the output of the rectifier drops below a restoration value less than the overvoltage value.

Figure 5:
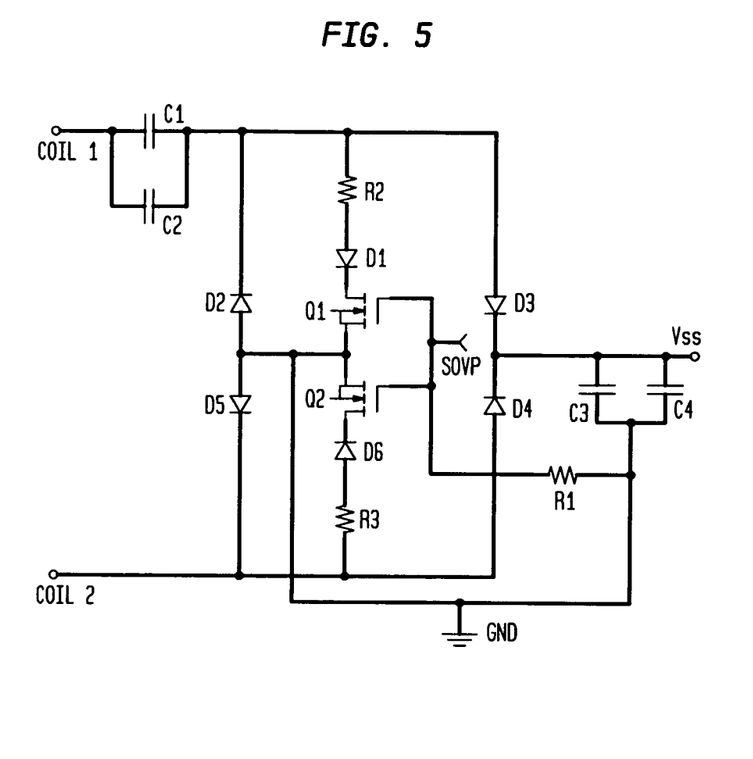
FIG. 5 is a schematic diagram illustrating components of bridge rectifier circuitry of an implanted module of a TET system in accordance with an embodiment of the invention.

As further shown in FIG. 4, the TET receiver 226 includes a set of bridge rectifiers and filters 414 for converting the form of the energy received at the secondary coil 124 from AC to DC. FIG. 5 is a schematic drawing showing the bridge rectifier and filter circuitry 414 in greater detail. The rectifier incorporates a set of diodes D2, D3, D4 and D5 connected in a bridge arrangement to receive the output of the secondary coil 124 for providing full-wave rectification of the transmitted AC power waveform. Two additional diodes D1 and D6 are blocking diodes to prevent FET body diode conduction when the clamp FETs Q1, Q2 are off. The gates of transistors Q1 and Q2 are connected through resistor R1 to ground, which keeps the transistors turned off when signal 411 is inactive.

All of the diodes shown in FIG. 5 can be Schottky diodes which are well-suited for rectifier applications, having relatively low on-resistance and turn-on voltages of about 0.2-0.3 V. Transistors Q1 and Q2 typically are n-type metal-oxide semiconductor field effect transistors (n-type MOSFETs), the sources of the transistors being connected to ground. Capacitors C1 and C2 series resonate with secondary coil 124 at the nominal drive frequency and are of low loss metalized plastic film construction. The capacitors are of equal value to evenly distribute the load current and losses to increase reliability. Capacitors can be selected for this purpose which are capable of handling relatively high current and voltage and which dissipate only small amounts of energy during normal operation. In one example, in order to provide operating margins and allow for transients, the capacitors may need to be capable of handling currents of several amperes and voltages of 600 V peak to peak or more. The second set of capacitors C3 and C4 may also include one electrolytic capacitor and another film capacitor having a smaller value, and these capacitors can operate to filter the rectified output voltage Vtet.

FIG. 4 further illustrates a current monitor circuit 420 coupled to bridge rectifier circuitry 414. The current monitor 420 provides input to the microcontroller 222. Highest current demands are during pump start up. When current detected by the current monitor 420 is excessive, the microcontroller 222 can provide a signal to a motor controller 222 or power manager 422 to reduce current demands.

Within the implanted module 120, a thermistor 424 may also be provided in close proximity to the housing 620 for detecting the module's temperature and providing a signal representative of the temperature to the microcontroller 222. If the temperature of the implanted module 120 becomes excessive, the microcontroller 222 can indicate the over-temperature condition to the external module 110 by outputting a signal thereto through the RF telemetry transceiver 224 or the backup telemetry transceiver 402.

Figure 6A:
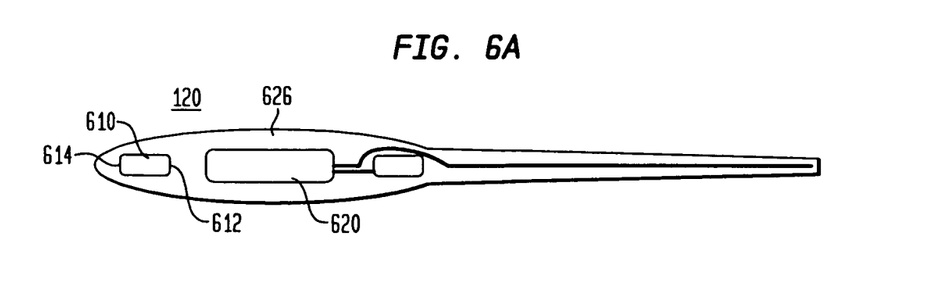
FIGS. 6A and 6B are perspective drawings illustrating placement and relationship of components of an implanted TET module viewed from an exterior surface in accordance with an embodiment of the invention.
Figure 6B:
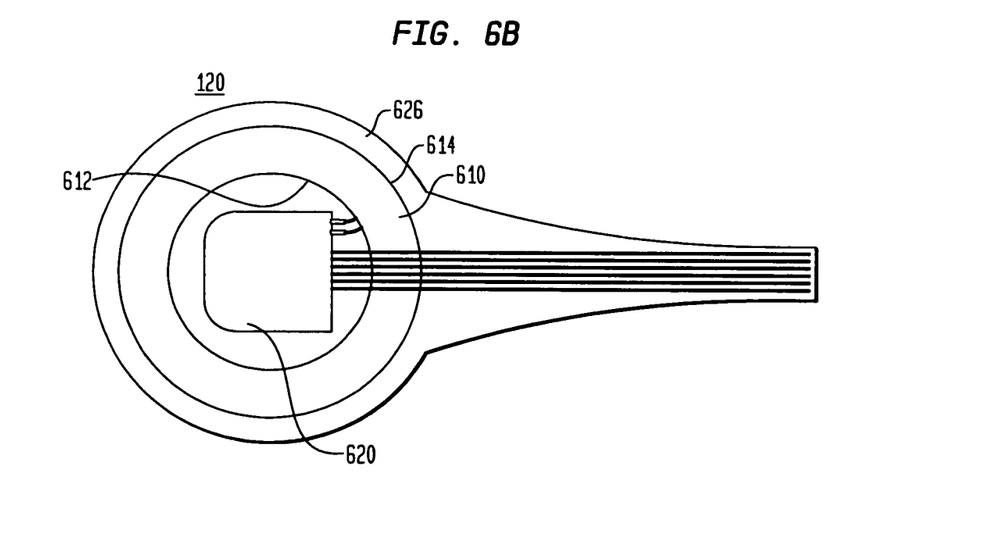

FIGS. 6A and 6B provides perspective diagram depicting an exterior of the implanted module 120. The secondary coil 124 can be fabricated in form of an oval or circular ring 610.

The bridge rectifier circuitry 414 and over voltage protection circuitry 408 can be hermetically encapsulated within a housing 620 which presents an exterior surface of biocompatible material. The housing 620 may fit within the inner wall 612 of the ring 610 as shown in FIG. 6. The housing 620 within the ring 610 may include a ceramic material to help distribute the heat generated by the bridge rectifier circuitry 414 so that temperature changes at the exterior of the implanted module 120 are gradual and limited to a small amount. An encapsulant 626 extending between the housing 620 and an outer wall 614 of the ring 610 can assist in spreading heat generated by the primary coil 124 and the bridge rectifier circuitry 414 over a greater volume. Providing the bridge rectifier circuitry 414 and the over voltage protection circuitry 408 inside the inner periphery of the ring may help to spread the heat generated by the coil 124 and the bridge rectifier circuitry 414 uniformly over these heat-generating elements.

In accordance with an embodiment of the invention, a method of operation of the TET system 100 will now be described. For some applications such as for supplying power to a VAD, the TET system 100 (FIG. 1) is intended to continually transfer power between the external module 110 and the implanted module 120; that is, during every second of each hour, every hour of the day and every day of the year. The flow of electrical power from the external module 110 to the implanted module 120 is precisely metered according to the instantaneous power demand of the VAD as monitored by the implanted module 120. Moreover, the amount of power transferred from the external module 110 to the implanted module 120 can be continuously adjusted at intervals of less than a second (e.g., from 50 times a second to 5000 times a second, for example) such that the implanted module 120 only receives as much power as it needs during such interval to power the implanted VAD or other therapeutic device 102. In that way, power is not drawn from the implanted battery 128 during normal operation of the VAD.

Stated another way, power is drawn from the implanted battery 128 generally only when there is an interruption in the transfer of power between the external 110 and implanted 120 modules or external power is deliberately disconnected, such as when the patient takes a shower. An interruption in power transfer can also occur when there is a gross movement of the patient that seriously affects coupling between the coils 114, 124 of the external 110 and implanted 120 modules, or when switching external power sources connected to the external module 110.

Thus, the microcontroller 222 rapidly samples (50 to 5000 times a second, for example) the voltage level Vtet on power supply line 412. The microcontroller 222 then causes RF telemetry transceiver 224 to communicate information back to the external module 110 which can be used in the external module 110 to ascertain the voltage level Vtet. For example, the microcontroller 222 may cause the transceiver 224 to transmit information in each communication to the external module 110 which directly indicates the voltage level Vtet.

Alternatively, the transceiver 224 can be used to transmit information merely indicating the voltage is higher or lower than the previously monitored value. In the case that transceiver 224 transmits the signal merely indicating the voltage level Vtet has increased, logic in the microcontroller 212 of the external module 110 can then determine the current voltage level Vtet by adding a fixed incremental value (e.g., 0.1 V) to the voltage level recorded just prior thereto. Otherwise, in the case that transceiver 224 transmits the signal merely indicating that the voltage level has decreased, logic in the microcontroller 212 of the external module 110 can then determine the current voltage level Vtet by subtracting a fixed incremental value (e.g., 0.1 V) from the voltage level recorded just prior thereto. Such sampling and reporting of results from the implanted module 120 to the external module 110 on a continuous, rapid and consistent basis allows the microcontroller 212 to maintain synchronized rapidly updated information indicating the variable voltage level Vtet in the implanted module 120.

Moreover, having synchronized rapidly updated information concerning the voltage level Vtet allows the external module 110 to supply power to the implanted module 120 according to the continuously changing power demand of the VAD or other implanted electrical device. An example of such operation can be seen in FIG. 7.

A patient's systemic blood pressure varies with time during the cardiac cycle. For this reason, a patient's blood pressure is usually expressed using two numbers, such as 115/75, for example. The higher number represents systolic blood pressure at maximum pressure reached because of the heartbeat. The lower number represents diastolic blood pressure at minimum pressure between heartbeats. Thus, once during each cardiac cycle the blood pressure rises to the systolic number with each heartbeat and falls again to the diastolic number before the next heartbeat.

Blood pressure and the flow of blood through the heart significantly and rapidly affect the load placed on a circulatory pump such as a VAD. Due to changes in load, the amount of current required for the pump to operate varies significantly during each cardiac cycle.

Figure 7:
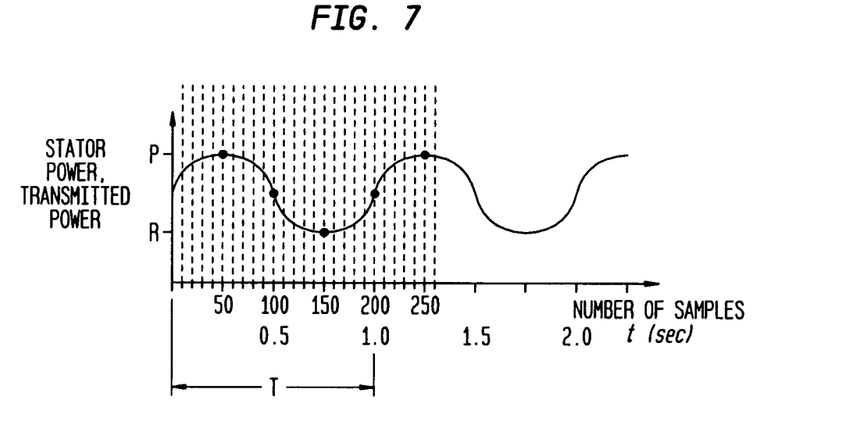
FIG. 7 is a graph illustrating a rate of feedback sampling and transmission of power between external and implanted modules of a TET system in a method of operation in accordance with an embodiment of the invention.

Referring to FIG. 7, a peak current ("P") is required to drive the motor stator of the VAD once during each cardiac cycle of pumping blood from the left ventricle into the aorta to pressurize the blood flowing into the aorta. The peak current is substantially greater than a reduced current value ("R") which is needed to drive the motor stator of the VAD at another time once during each cardiac cycle.

FIG. 7 indicates sampling intervals in which the voltage level Vtet is sampled. At a rapid sampling rate of 50 to 5000 samples per second, the voltage level is sampled 50 or more times per cardiac cycle, i.e., at the rate of 50 or more times per beat when the heart is beating at a rate of once per second, i.e., at 60 beats per minute. Therefore, FIG. 7 indicates that the voltage level has been sampled already 200 times by the time that one cardiac cycle ("T") has ended.

Because the power demand of the implanted VAD varies greatly (between P and R) during each cardiac cycle, power needs to be delivered to the implanted module 120 in a matching way. In order to fulfil this objective, the microcontroller 222 of the implanted module 120 samples the supply voltage Vtet and causes the RF telemetry transceiver 224 to transmit information back to the external module 110 for monitoring the implanted module's 120 internal supply voltage. If the internal supply voltage Vtet goes down, the implanted module 120 transmits a signal back to the external module 110. The external module 110 then transmits greater power to the implanted module 120, causing the internal supply voltage to rise towards the normal level. As indicated above, the external module 110 can vary power transmission in three ways. First, the external module 110 can vary the width of pulses during which power is transmitted by the primary coil 114. Secondly, the external module 110 might vary the frequency of such pulses, e.g., by a percentage of a carrier frequency depending upon coupling and load conditions. Thirdly, the external module 110 might also vary the power supply voltage Vs input to the TET driver 318 (FIG. 3). The external module 110 may vary the power transmitted via the primary coil 114 in one, two or all three of these ways in order to achieve the desired result in the implanted module 120. In turn, the implanted module 120 receives an amount of current (power) which is adjusted on a rapid and real-time basis in response to a monitored condition of the power circuit in the implanted module 120. In one example, one way that the amount of transmitted power can be adjusted is for the external module 110 to vary the primary drive pulse width of alternating current applied to the primary coil 114. Small changes in that pulse width can vary the amount of transmitted power significantly in accordance with the degree of resonance achieved in each of the primary 114 and secondary 124 coils.

On the other hand, if the internal supply voltage Vtet goes up, the implanted module 120 transmits a signal back to the external module 110. By reducing the primary drive pulse width, the external module 110 can transmit less power to the implanted module 120, causing the internal supply voltage to fall back towards a normal level.

Moreover, while the variation in power demand occurs as a function of the cardiac cycle, the rate of power transmission may also need to be varied according to the efficiency of transmission. Specifically, variations in coupling between the primary 114 and secondary 124 coils due to movement of the patient or interference, e.g., from objects or liquids (such as while bathing) can raise or lower the efficiency of power transmission. The monitored supply voltage information from the implanted module 120 can be used to raise or lower the power transmission rate to adjust for these changes in transmission efficiency related to coupling. In addition, whenever a strong change is detected in the voltage Vs of the external module 110 or Vtet of the implanted module 120, this can be a sign that the position of the primary coil 114 of the external module 110 has moved and needs adjusting. The external module 110 can then produce an audible, visible or tactile (e.g., vibrational) signal to the patient to indicate that the primary coil 114 positioning needs adjusting.

Whenever there is a problem in feeding back signals relating to the internal supply voltage Vtet to the external module 110 by way of the primary telemetry transceivers 224, 214, the backup telemetry system 402 can be used to transmit such information. When the backup telemetry system 402 is active, receiver 350 (FIG. 3) of the external module 110 "listens", i.e., picks up the signal from the primary coil 114 in intervals between individual power transmission pulses used to transmit power from the external module 110. In this way, rapid sampling and rapid adjustment of power transmission to the implanted module 120 can be maintained even when the primary telemetry transceivers 224, 114 are inoperable or transmission bandwidth is unavailable.

If the microcontroller 222 of the implanted module 120 senses an over-current condition via current monitor circuit 420, the telemetry system 224 or backup telemetry system 402 can be used to signal the event back to the external module 110. The rate of power transmission to the implanted module 120 can then be lowered or temporarily interrupted until the over-current condition is no longer present.

In a particular example of operation, the microcontroller 222 of the implanted module 120 may sense an over-temperature condition via a temperature sensor 424. In order for the implanted module 120 to remain comfortable to the patient, the temperature rise at the exterior surface of the implanted module 120 may need to be contained to one to two degrees Celsius. To lower the temperature in response to the over-temperature condition, the microcontroller 222 may temporarily reduce the current demand. For example, the microcontroller 222 can temporarily reduce the amount of current delivered to the motor or that is used for charging the implanted battery 128. When changing the amount of current used by the implanted module 120, the supply voltage Vtet may change. Changes in the supply voltage then are monitored and communicated to the external module 110 via the telemetry system 224 or backup telemetry system 402. The changes can then be addressed in a manner as described above such that the voltage Vtet is brought back within normal range.

Using thermistor 332, the external module 110 may also sense an over-temperature condition near the primary coil 114. As indicated above, the over-temperature condition may result from excessive current draw by the implanted module 120. To address the over-temperature condition, the microcontroller 212 of the external module 110 may transmit a signal to the implanted module 120 using the telemetry transceiver 214. In that way, the implanted module 120 can temporarily reduce the amount of current supplied to the motor or to the implanted battery 128 to cause the temperature to return to normal.

Figure 8:
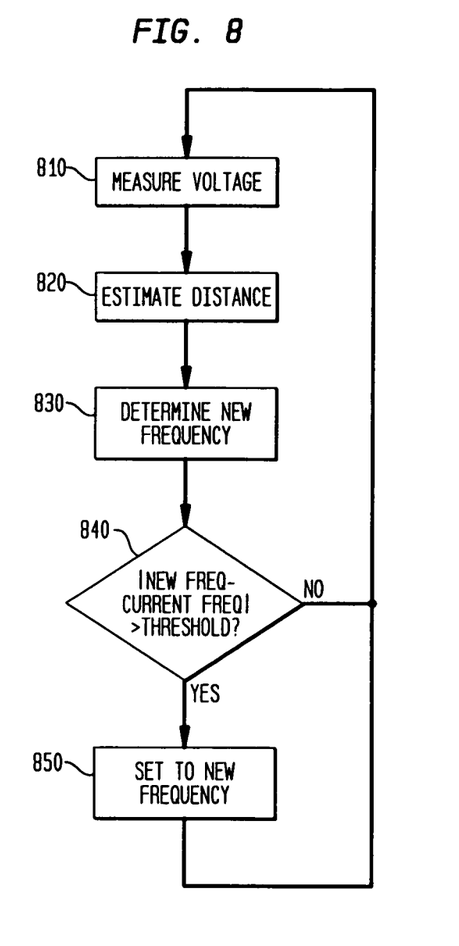
FIG. 8 is a flowchart illustrating a method of operation in accordance with an embodiment of the invention.

FIG. 8 is a flowchart illustrating a method of operation in accordance with an embodiment of the invention. In such embodiment, control is affected over the transmission frequency at which power is transmitted between the transmitting primary coil 114 of the external module 110 and the receiving secondary coil 124 of the implanted module 120. In such way, the transmission frequency can be maintained at a value which has a predetermined difference with respect to a resonant frequency of the power transmission system including the transmitting primary 114 and receiving secondary 124 coils. Thus, the variable transmission frequency can be adjusted to a value which is "near" (e.g., one to a few percent above or below) the resonant frequency, but not at the resonant frequency. Maintaining the transmission system at near resonance helps aid the stability of the system. When the system operates at the resonant frequency itself, a small change in the degree of coupling, i.e., the mutual inductance between the coils, can produce relatively large changes in the voltage across the transmitting primary 114 and receiving secondary 124 coils. The system may then require frequent adjustments to the voltage or current supplied to the transmitting primary coil 114 in order to stay within assigned operational limits.

On the other hand, when the system operates at a frequency near the resonant frequency but not at the resonant frequency, the system can operate with greater stability and power can be transmitted efficiently because the system may not need to be adjusted as frequently.

Thus, a parameter related to mutual inductance between the transmitting primary coil 114 and the receiving secondary coil 124 can be monitored. In one example, the parameter can include an estimate of the distance or displacement between the two coils. Using the monitored parameter, the variable transmission frequency can then be adjusted to a value which has a predetermined difference from the resonant frequency. In this way, the transmission frequency can be maintained with a predetermined difference, e.g., percentage difference, or absolute difference in frequency, from the resonant frequency between the transmitting primary 114 and receiving secondary 124 coils for the particular spatial displacement between the two coils.

In a particular embodiment (FIG. 8), a voltage across the transmitting primary coil 114 in the external module 110 is monitored (810). The measured voltage is an average voltage taken over a given period of time, for example 250 msec. This measured voltage helps to filter out variations in cardiac cycle. An increase in voltage can indicate greater spatial displacement between the transmitting primary 114 and receiving secondary 124 coils. For example, the voltage can increase when the external module 110 moves away from the implanted module 120, such as when the patient moves or bends. From the measured voltage, the distance between the two coils can be estimated (820). From the estimate of the distance, a new frequency value can be determined to which the transmission frequency should be adjusted. In a particular embodiment, the new transmission frequency can be determined (830) by using the estimated distance to look up the new transmission frequency value from a table stored in a memory of the external module 110. The new value is set to a frequency which has a predetermined difference from the resonant frequency of the system.

In one embodiment, the system operates with hysteresis in order to avoid frequent adjustments to the transmission frequency which might lead to instability. As indicated at step 840, a new value of the transmission frequency obtained by table look-up is compared to the current transmission frequency value to determine whether it is greater than a threshold amount. If the difference is greater than the threshold, the transmission frequency is set to the new value. (850) Operation then continues as before from step 810. However, if the difference between the new and current values is not greater than the threshold, the transmission frequency is not adjusted. Operation then continues as before from step 810.

Figure 9A:
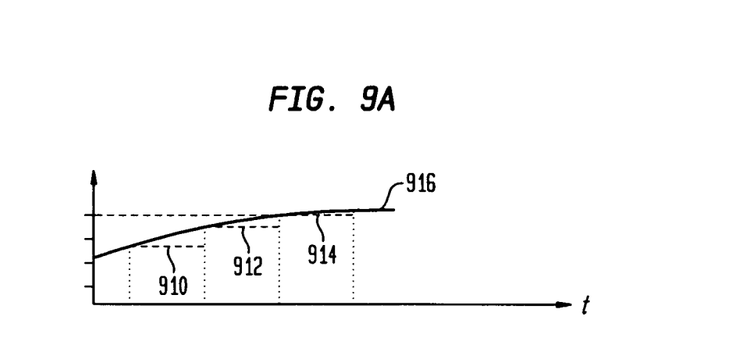
FIGS. 9A-C illustrate operation in accordance with a particular embodiment of the invention.
Figure 9B:
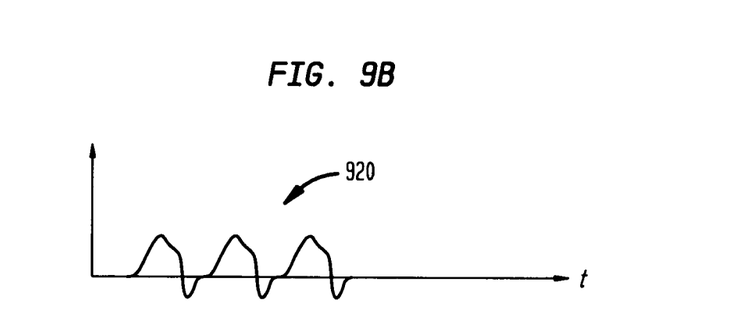
Figure 9C:
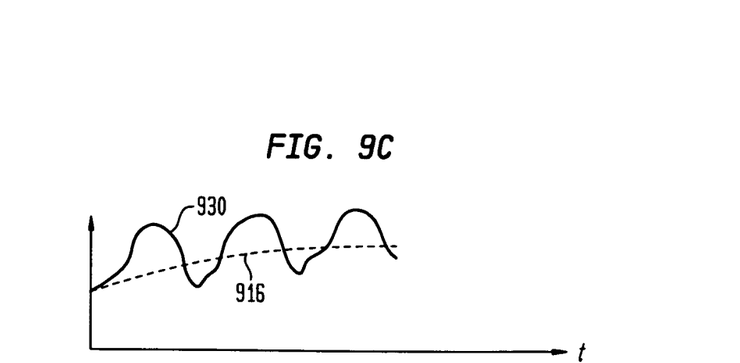

FIGS. 9A-9C illustrate operation in accordance with a variation of the embodiment described above with respect to FIG. 7. In this embodiment, a condition within the implanted module 120, e.g., power demand, is monitored relatively slowly, for example, just a few times each second or perhaps at intervals of one second or greater. For example, FIG. 9A illustrates measurements 910, 912, 914 of the power demand during successive intervals. In such case, the monitoring is insufficient to keep up with all changes in power demand during the cardiac cycle of the patient. Based upon the power measurements, a long-term power trend 916 can be estimated.

FIG. 9B illustrates a predictive signal 920. The predictive signal is a time-varying representative of a predicted change in power demand due to the cardiac cycle of the patient. The predictive signal can be based, for example, on a continuously obtained electrocardiogram ("EKG") reading taken of the patient by an appropriate device within the external module 110.

Based upon the long-term power trend 916 and the predictive signal 920, the microcontroller 212 can adjust the instantaneous amount of power to be supplied to the transmitting primary coil 114 such that a rapidly varying amount of power is transmitted as represented by curve 930 (FIG. 9C). The rapidly varying power curve 930 reflects both the long-term trend line 916 (shown in dashed form in FIG. 9C) and the rapidly-varying predictive signal.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

For example, in an implanted module 120 in accordance with a variation of the above-described embodiment (FIG. 3), the backup telemetry module 402 may include a radio frequency (RF) transmitter for transmitting signals to the external module 110 (FIG. 3). In this case, the backup telemetry module 402 can operate without having a coil (e.g., such as coil 406; FIG. 4) being inductively coupled with a primary coil 114 in the external module 110. In such variation, the RF transmitter of the backup telemetry module 402 can be designed to transmit signals over a frequency range different from that used by the primary RF transmitter 224 and avoid interference which affects the primary RF transmitter 224.

What is claimed is:

1. A circulatory assist device comprising:
   (a) a pump adapted for implant in a patient, the pump having an electric motor, the pump having a time-varying power demand which is adapted to vary with a cardiac cycle of the patient;
   (b) an implantable power unit adapted for mounting within a body of the patient, the implantable power unit having a secondary coil, a power circuit connected to the secondary coil for supplying power to the pump so that power applied to the secondary coil can be transmitted to the pump, and a monitoring circuit operable to monitor a condition of the power circuit and to send a transcutaneous telemetry signal representing the monitored condition,
   (c) an external power supply having a primary coil adapted for transcutaneous inductive coupling with the secondary coil, a drive circuit operable to apply an alternating current to the primary coil, and a control circuit operable to receive the telemetry signal and to adjust the alternating current in the primary coil at least in part in response to the telemetry signal,
   the monitoring circuit and control circuit being operable to monitor the condition of the power circuit and to adjust the alternating current in the primary coil in accordance therewith so as to vary the alternating current in the primary coil substantially in accordance with the cardiac cycle, and so as to vary an amount of the power applied to the secondary coil in accordance with the time-varying power demand of the pump in intervals of less than one second of a plurality of periodic intervals during the cardiac cycle, such that during each interval the external power supply is adapted to apply as much power to the secondary coil as needed to power the pump.

2. A circulatory assist device comprising:
   (a) an implantable pump adapted for mounting within the body of the patient, the pump having an electric motor with a time-varying power demand adapted to vary with a cardiac cycle of the patient;
   (b) an implantable power unit adapted for mounting within the body of the patient, the implantable unit having a secondary coil, a power circuit connected to the secondary coil for supplying power to the pump so that power applied to the secondary coil can be transmitted to the pump, and a monitoring circuit operable to monitor a condition being a voltage of the power circuit and to send a transcutaneous telemetry signal representing the monitored condition,
   (c) an external power supply having a primary coil adapted for transcutaneous inductive coupling with the secondary coil, a drive circuit operable to apply an alternating current to the primary coil, and a control circuit operable to receive the telemetry signal and to adjust the alternating current in the primary coil at least in part in response to the telemetry signal,
   wherein the control circuit is operable to adjust the alternating current in the primary coil in response to the telemetry signal so as to vary the alternating current in the primary coil substantially in accordance with the monitored condition and maintain the monitored condition in the power circuit within a desired range in each of a plurality of intervals during the cardiac cycle, each interval having a duration of less than one second.

3. A device as claimed in claim 1 or claim 2, wherein the monitoring and control circuit are operable to monitor the condition of the power circuit in response to a change in coupling between the primary and secondary coils and adjust the alternating current in the primary coil so as to vary the alternating current in the primary coil substantially in accordance with the change in coupling and maintain the monitored condition within the desired range despite the change in coupling.

4. A device as claimed in claim 1 or claim 2, wherein the monitoring circuit is arranged to monitor the condition of the power circuit and to send the telemetry signal at least 50 times per second.

5. A device as claimed in claim 1 or claim 2, wherein the monitored condition includes a voltage supplied by the secondary coil.

6. A device as claimed in claim 1 or claim 2, wherein the power circuit includes a rectifier having an input and an output and the monitored condition includes a voltage at the output of the rectifier.

7. A device as claimed in claim 6, further comprising a non-ferromagnetic ceramic housing containing the rectifier.

8. A device as claimed in claim 6, wherein the rectifier is a Schottky diode bridge rectifier.

9. A device as claimed in claim 6, wherein the power circuit of the implantable unit further includes an overvoltage protection element operable to connect a shunt across the input of the rectifier if the voltage at the output of the rectifier exceeds a predetermined overvoltage value, the overvoltage protection element being operable to disable the power circuit if the voltage at the output of the rectifier exceeds the overvoltage value and re-enable the power circuit if the voltage at the output of the rectifier drops below a restoration value less than the overvoltage value.

10. A device as claimed in claim 1 or claim 2, wherein the power circuit further includes a battery and a routing circuit arranged to route power from the secondary coil to the motor, to the battery or both when power is received through the secondary coil and from the battery to the motor when power is not received by the secondary coil, and wherein the monitoring circuit and control circuit are operable to vary the current in the primary coil so as to maintain the condition within the desired range during the charging operation and during operation when the battery is fully charged.

11. A device as claimed in claim 1 or claim 2, wherein the monitoring circuit further includes a temperature sensor operable to detect a temperature within the implantable power unit.

12. A device as claimed in claim 11, wherein the monitoring circuit is arranged to reduce a supply of current by the power circuit to at least one of the pump or an implanted battery coupled to the implantable power unit when the detected temperature exceeds a threshold.

13. A device as claimed in claim 1 or claim 2, wherein the drive circuit is operable to apply the alternating current to the primary coil at a first frequency, and the monitoring circuit is operable to send the telemetry signal at a frequency different from the first frequency.

14. A device as claimed in claim 13, wherein the monitoring circuit includes a first transmitter and a second transmitter and is operable to send a first telemetry signal via the first transmitter and is operable to send a second telemetry signal via the second transmitter when there is a problem in transmitting the first telemetry signal.

15. A device as claimed in claim 13, wherein the control circuit is operable to automatically adjust the first frequency to adjust a resonance between the primary and secondary coils for efficient and stable transmission of power between the primary and secondary coils.

16. A device as claimed in claim 15, wherein the control circuit is operable to receive the telemetry signal and to adjust the alternating current in the primary coil at a sufficient rate such that the implantable power unit can operate without an implanted battery for supplying power to the pump.

17. The circulatory assist device of claim 1 or claim 2, wherein the monitoring circuit and the control circuit are operable to vary an amount of the power applied to the secondary coil in the intervals in accordance with the time-varying power demand of the pump unless there is an interruption in transfer of power between the external power supply and the implantable power unit.

18. A circulatory assist device comprising:
(a) a pump adapted for implant in a patient, the pump having an electric motor with a time-varying power demand which is adapted to vary substantially in accordance with a cardiac cycle of the patient;
(b) an implantable power unit adapted for mounting within the body of the patient, the implantable power unit having a secondary coil, a power circuit connected to the secondary coil for supplying power to the pump so that power applied to the secondary coil can be transmitted to the pump, and a monitoring circuit operable to monitor a condition of the power circuit and to send a transcutaneous telemetry signal representing the monitored condition at periodic intervals of less than one second during the cardiac cycle,
(c) an external power supply having a primary coil adapted for transcutaneous inductive coupling with the secondary coil, a drive circuit operable to apply an alternating current to the primary coil, a receiver operable to receive the telemetry signal, a prediction circuit operable to generate a predictive signal estimating an instantaneous power demand of the pump based upon the received telemetry signal and a signal representing at least the heartbeat of the patient, a control circuit operable to adjust the alternating current in the primary coil at least in part in response to the received telemetry signal and the predictive signal, so as to maintain the monitored condition within a desired range substantially throughout the cardiac cycle, such that during each interval the external power supply is adapted to apply as much power to the secondary coil as needed to power the pump.

* * * * *